United States Patent [19]
Han et al.

[11] Patent Number: 4,559,343
[45] Date of Patent: Dec. 17, 1985

[54] NONIRRITATING AQUEOUS OPHTHALMIC COMPOSITIONS COMFORT FORMULATION FOR OCULAR THERAPEUTIC AGENTS

[75] Inventors: Wesley W. Han, Mansfield; Robert E. Roehrs, Fort Worth, both of Tex.

[73] Assignee: Alcon Laboratories, Inc., Fort Worth, Tex.

[21] Appl. No.: 415,758

[22] Filed: Sep. 7, 1982

[51] Int. Cl.$^4$ ............................................. A61K 31/52
[52] U.S. Cl. .................................. 514/264; 514/914; 514/974
[58] Field of Search ................ 424/253; 514/264, 914, 514/974

[56] References Cited

U.S. PATENT DOCUMENTS

| 2,994,640 | 8/1961 | Zellner ................................ 424/253 |
| 3,439,094 | 4/1969 | Emele .................................. 424/253 |
| 3,632,742 | 1/1972 | Eckert et al. ........................ 424/253 |
| 3,957,994 | 5/1976 | Schroer .............................. 424/253 |
| 4,141,976 | 2/1979 | Voorhees ........................... 424/253 |
| 4,420,483 | 12/1983 | Sunshine et al. .................... 424/253 |

FOREIGN PATENT DOCUMENTS 56-97224  5/1981  Japan ................................... 424/253

OTHER PUBLICATIONS

J. Pharm. Exp. Thera. 198(2) 481-488 (1976)—Bito et al.
Chem. Abst. 77, 9594(u) (1972)—Riviere.
Chem. Abst. 84, 130,369(x) (1976)—Bourillet et al.
Chem. Abst. 95, 18119(s) (1981)—Fujimura et al.
Abstract B-5 ReBE-897, 356-A and 22.07.82 US 400, 597.

Primary Examiner—Douglas W. Robinson
Attorney, Agent, or Firm—Fitch, Even, Tabin & Flannery

[57] ABSTRACT

Xanthine derivatives are described which decrease the stinging associated with the application of ophthalmic acidic anti-inflammatory agents.

7 Claims, No Drawings

NONIRRITATING AQUEOUS OPHTHALMIC COMPOSITIONS COMFORT FORMULATION FOR OCULAR THERAPEUTIC AGENTS

This invention relates generally to aqueous ophthalmic compositions for treatment of the eye, and more particularly, it relates to nonirritating aqueous ophthalmic compositions containing aryl- and heteroarylcarboxylic acids, aryl- and heteroarylalkanoic acids and therapeutic agents which compositions contain an effective amount of a xanthine derivative which elminates or reduces discomfort with acid containing ophthalmic drugs.

Steroidal anti-inflammatory agents are useful therapeutic agents, but are known for their undesirable side effects including, but not limited to, salt retention, edema, and potential danger to pregnant women. To avoid these undesirable side effects non-steroidal, anti-inflammatory agents such as aryl- and heteroarylcarboxylic acids and aryl- and heteroarylalkanoic acids and pharmaceutically acceptable salts of such acids may be used. However, it has not been possible to formulate these acidic anti-inflammatory agents in aqueous ophthalmic compositions because the acids disassociate in aqueous solution forming soap like compounds which cause severe ocular discomfort including stinging and excessive tear generation. In addition to the discomfort to the patient caused by the stinging sensation, the excess tears generated may also dilute and/or wash away the drug from the ocular surface.

Attempts to decrease ocular stinging of non-steroidal acidic anti-inflammatory agents through conventional formulation approaches have not proved successful. Aqueous solutions of suprofen and ketoprofen, two recognized non-steroidal acidic anti-inflammatory agents, when formulated with different ophthalmic preservatives such as benzalkonium chloride, chlorobutanol, and thimerosal provide little or no reduction in the stinging or discomfort caused when these drugs are instilled into the eye in aqueous solution. Likewise changing buffering agents, such as sodium phosphate, sodium borate, and sodium citrate, and their concentrations provides little or no reduction in stinging. Changing the cations in solution from sodium to potassium gives rise to some improvement in reduction of the stinging effect, but not to a satisfactory level. Incorporating inert adjuvants such as polyvinyl alcohol, glycerin, glycine and ethyl alcohol provides little or no reduction of the stinging or discomfort of the acidic anti-inflammatory agent. Varying the pH of the ocular solutions provides little or no reduction of discomfort.

A need exists, therefore, for a non-steroidal, anti-inflammatory composition which has the advantages of not being a steroid, and which may be used in the topical treatment of diseases of the eye without producing stinging or ocular discomfort. More particularly, a need exists for a formulation of aryl- and heteroarylcarboxylic acids or aryl- and heteroarylalkanoic acids and pharmaceutically acceptable salts thereof which with topical ocular use will not produce discomfort.

It has been found that methyl and ethyl derivatives of xanthine when formulated in an aqueous non-steroidal, anti-inflammatory composition containing aryl- and heteroarylcarboxylic acids or aryl- and heteroarylalkanoic acids or mixtures thereof, results in a composition that may be applied topically to the eye with little or no discomfort previously known with the use of such agents.

The xanthine derivatives which have been found to be effective in reducing ocular discomfort in accordance with the present invention are those having the following structure:

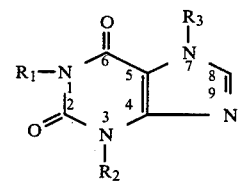

Where $R_1$, $R_2$ and $R_3$ are either hydrogen, methyl or ethyl, and at least two of $R_1$, $R_2$ and $R_3$ are methyl or ethyl. Theophylline, which has methyl groups at the 1 and 3 positions, caffeine, which has methyl groups at the 1, 3, and 7 positions, and theobromine, which has methyl groups at the 3 and 7 positions are examples of xanthine derivatives contemplated by the present invention.

These derivatives when added to a finished buffered isotonic aqueous composition of aryl- and heteroarylcarboxylic acids and/or aryl- and heteroarylalkanoic acids or pharmaceutically acceptable salts of such acids with the concentration of the derivative at an upper level of about the solubility of the xanthine derivative to a lower limit which is function of the dosage of and how much stinging or discomfort the anti-inflammatory agent causes, with the lower concentration limit of the xanthine derivative preferably 0.05% by weight/volume of the aqueous composition, will provide an ocular anti-inflammatory agent which can be topicaly applied with little or no discomfort or ocular stinging to the patient. Ingredients including but not limited to benzalkonium chloride, thimerosal, NaCl and buffering agents may be optionally added to the composition as is known in the art. It is readily apparent that the amount of xanthine derivatives will vary depending on the particular acid drug used and the amount of drug in the composition.

There are a large number of acidic anti-inflammatory agents which can be incorporated in compositions in accordance with the present invention. Examples of aryl- or heteroarylcarboxylic acids include mefenamic acid or 2-[(2,3-dimethylphenyl)amino]benzoic acid, flufenamic acid or 2[[3-(trifluoromethyl)phenyl]amino]-benzoic acid, clonixin or 2-(3-chloro-o-toluidino)nicotinic acid and flufenisal or 4' fluoro-4-acetate-biphenyl-3 carboxylic acid.

Examples aryl- or heteroarylalkanoic acids include 4-(t-butyl)benezeneacetic acid, ibufenac or 4-(2-methylpropyl)benezeneacetic acid, ibuprofen or α-methyl-4-(2 methylpropyl)benezeneacetic acid, alclofenac or 3-chloro-4-(2-propenyloxy)benzeneacetic acid, fenoprofen or α-methyl-3-phenoxybenzeneacetic acid, naproxen or 2-(6-methoxy-2-naphthyl)propionic acid, indomethacin or 1-(p-chlorobenzoyl)-5-methoxy-2-methylindole-3-acetic acid, tolmetin or 1-methyl-5-(4-methylbenzoyl)-1H-pyrrole-2-acetic acid, flurbiprofen or 2-fluoro-α-methyl [1,1'-biphenyl]-4-acetic acid, ketoprofen or 2-(3-benzoylphenyl)propionic acid, namoxyrate or 2-(p-biphenylyl)butyrate dimethylaminoethanol salt and suprofen or para-2-thenoylhydratropic acid.

The acidic anti-inflammatory agent may be incorporated in the ophthalmic composition in accordance with known practices in order to provide an effective rate of delivery of the therapeutic agent to the eye when applied topically. For example, the ophthalmic composition may contain between about 0.5 percent and about 3.0 percent by weight/volume suprofen. The exact amount of anti-inflammatory agent will depend upon the particular anti-inflammatory agent selected and the strength of the ophthalmic composition. Further, additional therapeutic agents including steroids such as dexamethazone, antibiotics such as gentamicin, antiinfectives such as sulfonamides, and antiallergics such as antihistamines may be added to and supplement the ophthalmic composition as is known.

The compositions may contain preservatives such as thimerosal, chlorobutanol, benzalkonium chloride, or chlorhexidine, buffering agents such as phosphates, borates, carbonates and citrates, and thickening agents such as high molecular weight carboxy vinyl polymers such as the ones sold under the name of Carbopol which is a trademark of the B. F. Goodrich Chemical Company, hydroxymethylcellulose and polyvinyl alcohol, all in accordance with the prior art.

The compositions are prepared by dissolving the various ingredients in the required amount of water with stirring to insure that all the ingredients are dissolved. The aqueous compositions of the invention may be solutions, suspensions, or gels. After preparation of the solution, suspension, or gel the compositions are then packaged in dispensers suitable for delivery of the ophthalmic composition.

The following examples of ophthalmic compositions typify the manner in which the invention may be practiced. The examples should be construed as illustrative, and not as a limitation upon the overall scope of the invention. The percentages are expressed on a weight/volume basis.

EXAMPLE I

| Suprofen 0.5% Solution With Benzalkonium Chloride | |
|---|---|
| Suprofen | 0.5% + 5% excess of the drug |
| Caffeine | 1.0% |
| Pluronic F127* | 0.5% |
| Benzalkonium Chloride | 0.01% + 10% excess |
| Disodium Edetate | 0.1% |
| Dried Sodium Phosphate | 0.1% |
| Sodium Biphosphate | 0.03% |
| Sodium Chloride | 0.6% |
| pH adjustment with NaOH or HCl | q.s. pH 7.4 |
| Purified Water | q.s. 100% |

*a high molecular weight non-ionic surfactant sold under the registered trademark of the Wyandotte Chemicals Corp.

EXAMPLE II

| Indomethacin 0.5% Suspension | |
|---|---|
| Indomethacin | 0.5% plus a 5% excess of the 0.5% drug |
| Caffeine | 1.0% |
| Thimerosal | 0.005% plus a 10% excess of the Thermerosal |
| Disodium Edetate | 0.1% |
| Sodium CHloride | 0.7% |
| Tyloxapol | 0.1% |
| Dried Sodium Phosphate | 0.1% |

| -continued | |
|---|---|
| Indomethacin 0.5% Suspension | |
| Sodium Biphosphate | 0.03% |
| pH adjustment with NaOH or HCl to pH of 7.4 | q.s. pH 7.4 |
| Purified Water | q.s. 100% |

EXAMPLE III

| Melofenamic Acid 0.1% Suspension | |
|---|---|
| Melofenamic Acid | 0.1% plus a 5% excess of the 0.1% drug |
| Caffeine | 1.0% |
| Thimerosal | 0.005% plus a 10% excess of the 0.005% Thimerosal |
| Disodium Edetate | 0.1% |
| Dried Sodium Phosphate | 0.1% |
| Sodium Biphosphate | 0.03% |
| Sodium Chloride | 0.7% |
| pH adjustment with HCl or NaOH to a pH of 7.4 | q.s. pH 7.4 |
| Purified Water | q.s. 100% |

EXAMPLE IV

| Ketoprofen Solution | |
|---|---|
| Ketoprofen | 0.25% |
| Theophylline | 0.5% |
| Thimerosal | 0.01% |
| Sodium Biphosphate | 0.03% |
| Dried Sodium Phosphate | 0.1% |
| Sodium Chloride | 0.65% |
| Diethanolamine | 0.25% |
| DiSodium Edetate | 0.01% |
| pH adjustment with NaOH or HCl to a pH of 7.4 | q.s. pH 7.4 |
| Purified Water | q.s. 100% |

EXAMPLE V

| Flurbiprofen | |
|---|---|
| Flurbiprofen | 0.5% |
| Caffeine | 1% |
| Thimerosal, | 0.005% |
| Disodium Edetate, | 0.1% |
| Dried Sodium Phosphate, | 0.1% |
| Sodium Chloride, | 0.7% |
| pH adjustment with HCl or NaOH to pH 7.4 | q.s. 7.4 |
| Purified Water, | q.s. 100% |

It should be understood that while certain preferred embodiments of the present invention have been illustrated and described, various modifications thereof will become apparent to those skilled in the art. Accordingly, the scope of the present invention should be defined by the appended claims and equivalents thereof.

Various features of the invention are set forth in the followng claims.

What is claimed is:

1. An aqueous, nonirritating, nonsteroidal, ophthalmic composition for topical application to the eye comprising:

a therapeutically effective amount of suprofen for topical treatment of inflammation of the eye, and pharmaceutically acceptable salts thereof;

a xanthine derivative being present in an amount between the amount of derivative soluble in the water of said composition and 0.05% by weight/volume of said composition which is effective to reduce the discomfort associated with suprofen upon topical application of said composition, said xanthine derivative being selected from the group consisting of theophylline, caffeine, theobromine and mixtures thereof;

an ophthalmic preservative; and a buffer, to provide an isotonic, aqueous, nonirritating nonsteroidal ophthalmic composition.

2. An aqueous, nonirritating, nonsteroidal, ophthalmic composition as recited in claim 1 wherein said xanthine derivative is caffeine.

3. An aqueous, nonirritating, nonsteroidal ophthalmic composition as recited in claim 2 wherein said suprofen comprises between about 0.5 to about 3.0 percent by weight/volume of said ophthalmic composition.

4. A method for reducing the stinging and discomfort associated with the topical application to the eye of an aqueous solution of a therapeutically effective amount of anti-inflammatory agent for topical treatment of inflammation of the eye, said agent selected from the group consisting of mefenamic acid, flufenamic acid, clonixin, flufenisal, 4-(t-butyl)benzeneacetic acid, ibufenac, ibuprofen, alclofenac, feneprofen, naproxen, indomethacin, tolmetin, flurbiprofen, ketoprofen, namoxyrate, suprofen, pharmaceutically acceptable salts of the foregoing acids and mixtures thereof, said method comprising adding to said aqueous solution an xanthine derivative in an amount between the amount of derivative soluble in the water of said composition and 0.05% by weight/volume of said composition which is effective to reduce the discomfort associated with said anti-inflammatory agent upon said topical application, said xanthine derivative having the formula

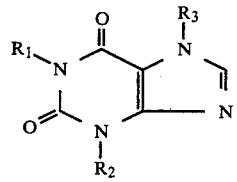

where each of $R_1$, $R_2$ and $R_3$ is selected from hydrogen, methyl and ethyl, and at least two of $R_1$, $R_2$ and $R_3$ are selected from methyl and ethyl, and mixtures thereof forming a nonirritating ophthalmic composition.

5. A method as recited in claim 4 wherein said xanthine derivative is selected from the group consisting of theophylline, caffeine, theobromine and mixtures thereof.

6. A method as recited in claim 5 wherein said anti-inflammatory agent is suprofen and said xanthine derivative is caffeine.

7. A method as recited in claim 6 wherein said suprofen comprises between about 0.5 to about 3.0 percent by weight/volume of said ophthalmic composition.

* * * * *